United States Patent
Eustergerling et al.

(10) Patent No.: US 7,633,071 B2
(45) Date of Patent: Dec. 15, 2009

(54) IMAGE SENSOR FOR A FLUORESCENCE SCANNER

(75) Inventors: Norbert Eustergerling, Erlangen (DE); Donal Medlar, Weisendorf (DE); Volker Pritsching, Erlangen (DE); Wolfgang Strob, Erlangen (DE)

(73) Assignee: Siemens Aktiengesellschaft (DE)

( * ) Notice: Subject to any disclaimer, the term of this patent is extended or adjusted under 35 U.S.C. 154(b) by 39 days.

(21) Appl. No.: 11/376,583

(22) Filed: Mar. 15, 2006

(65) Prior Publication Data

US 2006/0268402 A1    Nov. 30, 2006

(30) Foreign Application Priority Data

Mar. 18, 2005  (DE)  .......................  10 2005 013 044

(51) Int. Cl.
*G02B 21/06* (2006.01)
(52) U.S. Cl. ................................... 250/458.1
(58) Field of Classification Search ............... 250/484.4
See application file for complete search history.

(56) References Cited

U.S. PATENT DOCUMENTS

| 4,951,133 | A |   | 8/1990 | Onoda |
| 5,965,875 | A | * | 10/1999 | Merrill ....................... 250/226 |
| 6,377,700 | B1 |  | 4/2002 | Mack et al. |
| 2003/0139661 | A1 |  | 7/2003 | Kimch et al. |
| 2003/0191368 | A1 |  | 10/2003 | Wang et al. |
| 2004/0031931 | A1 |  | 2/2004 | Mueller et al. |
| 2004/0037454 | A1 |  | 2/2004 | Ozawa et al. |
| 2004/0169854 | A1 |  | 9/2004 | Vo-Dinh et al. |
| 2004/0249245 | A1 |  | 12/2004 | Irion |
| 2005/0027166 | A1 |  | 2/2005 | Matsumoto et al. |
| 2005/0068534 | A1 |  | 3/2005 | Kleinfeld et al. |
| 2005/0073729 | A1 |  | 4/2005 | Schmid et al. |
| 2005/0148842 | A1 |  | 7/2005 | Wang et al. |
| 2005/0285038 | A1 | * | 12/2005 | Frangioni ................... 250/330 |

FOREIGN PATENT DOCUMENTS

| DE | DE 1999 83 341 T1 | 1/2000 |
| EP | 1 374 755 A1 | 1/2004 |
| WO | WO 97/33157 | 9/1997 |

(Continued)

OTHER PUBLICATIONS

Novadaq Technologies Inc.: "SPY Intra-operative Imaging System", 2 pages; printed on Feb. 7, 2006 and located at http://www.novadaq.com/spy_imaging_system.php.

(Continued)

*Primary Examiner*—David P Porta
*Assistant Examiner*—Marcus H Taningco
(74) *Attorney, Agent, or Firm*—Brinks Hofer Gilson & Lione

(57) ABSTRACT

An image sensor for a fluorescence scanner for recording both optical and fluorescence images is described. The image sensor includes an image detector and a filter layer. The filter layer comprises at least two different surface portions which have at least two different filter properties. At least one surface portion has a filter characteristic such that fluorescent light can pass through, and at least visible light is filtered out. At least one further surface portion has a filter characteristic such that visible light can pass through.

13 Claims, 3 Drawing Sheets

FOREIGN PATENT DOCUMENTS

WO    WO 03/105485 B1    12/2003

OTHER PUBLICATIONS

U. Mahmood et al., Near-Infrared Optical Imaging of Protease Activity for Tumor Detection; Radiology vol. 213, No. 3; pp. 866-870 and Dec. 1999.

A. Hengerer et al. "Molecular Biology for Medical Imaging," Electromedia vol. 69, No. 1; pp. 44-49; 2001.

http://www.ehendrick.org/healthy/001004.htm; printed on Feb. 7, 2006; 2 pages.

"New Multichannel Fluorescence Reflectance Imaging System for Small Animal Applications," by A. Wall et al.; European radiology, 2003, Supplement to vol. 13, p. 303.

"Multispectral Fluorescence Imager May Guide Surgical Procedure," by B.D. Butkus; Biophotonics, vol. 10, No. 4; pp. 18-19; May 2003.

Cri Products: In-Vivo Imaging, & Fluorescence Microscopy website pages; located at http://www.cri-inc.com/products/index.asp; 10 pages and printed on Dec. 22, 2005.

"Imaging Enzyme Activity and Gene expression in Vivo Through a 2.7F Catheter Feasibility Study in Mice," by M. Funovics et al.; Radiology vol. 231, No. 3; pp. 659-666 and Jun. 2004.

Xillix—Seeing Cancer in a New Light; Xillix Technologies Corp.; located at http://www.xillix.com/index_home.cfm; printed on Feb. 7, 2006 and 1 page.

* cited by examiner

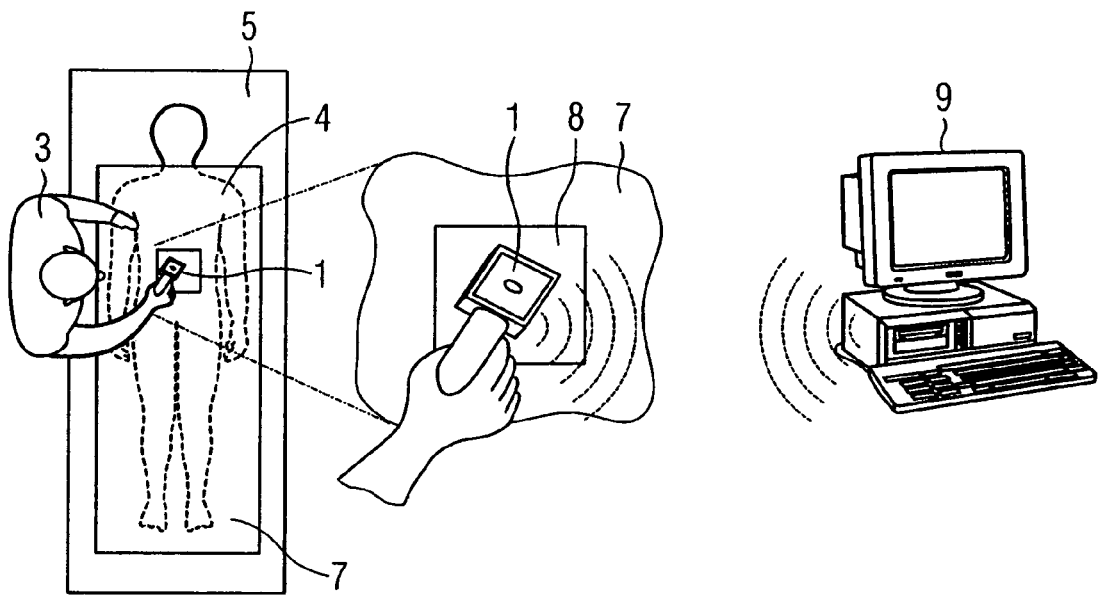
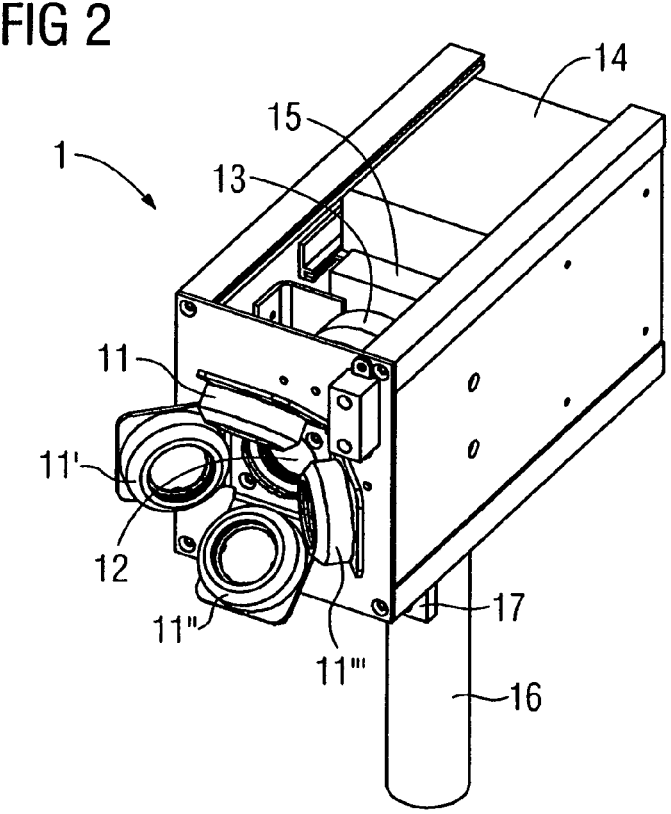

IMAGE SENSOR FOR A FLUORESCENCE SCANNER

RELATED APPLICATIONS

This application claims the benefit of German Patent application DE 10 2005 013 44.5, filed on Mar. 18, 2005, which is incorporated herein by reference.

This application relates an image sensor for a fluorescence scanner, and to a fluorescence scanner incorporating an image sensor.

BACKGROUND

Equipment for fluorescence detection, hereinafter also called fluorescence scanners, can be used to detect the most various molecular factors. Substances having different molecular properties can have different fluorescent properties, which can be detected in a targeted way. The fluorescence detection is optically based and hence is noninvasive or only minimally invasive. With the knowledge of the applicable fluorescent properties, it is possible to ascertain the molecular nature of a given material being examined.

In medicine, molecular properties, which may be termed a "molecular signature", provide information about the state of health of a living creature or patient and can therefore be assessed diagnostically. Molecular signatures can be used in particular for detecting cancer. Still other syndromes, such as rheumatoid arthritis or arteriosclerosis of the carotid artery, can thus be identified.

Fluorescence detection, fluorescence may be excited, which by optical excitation. The excitation light can be in the infrared range (IR), for example, or in the near infrared range (NIR). The suitable optical frequency range is also dependent on the substance to be examined. Those substances having no molecular or chemical properties suitable for fluorescence detection can be molecularly "marked". For example, markers that with suitable preparation bind to or to be deposited only on very special molecules can be used. Such marking functions by a mechanism that, in pictorial terms, can be thought of as a lock-and-key mechanism. The marker and the molecule to be detected fit one another like a lock and key, while the marker does not bind to other substances. If the marker has known fluorescent properties then, after the binding or deposition, the marker can be optically detected. The detection of the marker then allows conclusions to be drawn as to the presence of the marked special substance. For detection, accordingly only one detector is needed, being capable of detecting light in the wavelength that the substance in question, or the marker used, emits upon excitation.

Such fluorescence methods may be used for examinations of regions near the surface or examinations in the open body (intra-operative applications). Examples of such investigations would be detecting fluorescently marked skin cancer or the detection of tumor boundaries in the resection of fluorescently marked tumors. For example, a system for making coronary arteries and the function of bypasses (that is, the blood flow through them) visible intra-operatively has been developed.

One subject of research in biotechnology is fluorescent metabolic markers that accumulate only in certain regions (such as tumors, infections, or other foci of disease), or are distributed throughout the body but are activated only in certain regions. For example, activation is by tumor-specific enzyme activities or, for example, by additional exposure to light.

In medical diagnosis, as marker substances, so-called fluorophores such as indocyanin green (ICG) are known, which for example bind to blood vessels and can be detected optically, so that in an imaging process, the contrast with which blood vessels are displayed can be enhanced. So-called "smart contrast agents" are also becoming increasingly important. Activatable fluorescence markers may bind for example to tumor tissue and the fluorescent properties are not activated until the binding to the substance to be marked occurs. Such substances may comprise self-quenched dyes, such as Cy5.5, which are bound to larger molecules by way of specific peptides. The peptides can in turn be detected by means of specific proteases, produced for example in tumors, and can be cleaved. The fluorophores are released by the cleavage and are no longer self-quenched but instead develop their fluorescent properties. The released fluorophores can be activated for example in the near IR wavelength range of around 740 nm. One example of a marker on this basis is AF 750 (Alexa Fluor 750), with a defined absorption and emission spectrum in the wavelength range of 750 nm (excitation) and 780 nm (emission).

In medical diagnosis, such activatable markers can be used for example for intra-operative detection of tumor tissue, so that the diseased tissue can be identified exactly and then removed. One typical application is the surgical treatment of ovarian cancer. Here, the diseased tissue is typically removed surgically, and the patient later treated by chemotherapy. Because of the increased sensitivity of fluorescence detection, the diseased tissue can be better detected along with various surrounding foci of disease and thus removed more completely.

In the treatment of breast cancer, typical surgical treatments are lumpectomies (or mastectomies) and lymph node sections and lymph node biopsies. Lymph nodes are typically detected optically by means of 99 mTc sulfur colloids in combination with low-molecular methylene blue. The radioactive mTc sulfur colloids could be avoided by using fluorescence detection, with correspondingly favorable effects on the health of the patient.

In the removal of brain tumors, the precise demarcation of the tumor tissue, which is attainable by the use of fluorescence detection, is of obvious importance. The treatment of pancreatic tumors can benefit from additional lymph node biopsies which could be identified by fluorescence detection, to detect possible intestinal cancer. In the treatment of skin cancer, the detection of skin neoplasms could be improved by fluorescence detection. The treatment of rheumatoid arthritic diseases of joints could improve medication monitoring in the sense that the extent of protease overproduction could be detected quantitatively, and the medication provided to counteract protease overproduction could be adapted quantitatively.

In treating these diseases which are identified as examples as well as other syndromes, an operation may be performed in which the diseased tissue is removed surgically. Fluorescence detection can be performed, to improve the detection of the diseased tissue portions to be removed during an ongoing operation, in the open wound. The tissue parts are marked before the operation with a suitable substance that is then activated by binding to the diseased tissue parts. An apparatus for fluorescence detection should therefore be easy for the surgeon to manipulate and should be usable in the sterile field of the operating room.

The detection of a region marked fluorescently in this way is done by exposing the region to light in the particular excitation wavelength of the fluorescent dye, and detecting the emitted light in the corresponding emission wavelength of the fluorophore. A fluorescence scan is made by recording a fluorescence image based on fluorescent light along with an optical image based on visible light. Next, the optical image and the fluorescence image are superimposed, in order to display the fluorescence in the context of the visual image. From the superimposed view (fusion) of the optical and fluorescence images on a display device, the surgeon can detect the tumor tissue and locate it in the body of the actual patient. The fused image with the fluorescently marked tissue is displayed on a screen on the fluorescence scanner or on an external computer with image processing software.

Typically, the excitation of the fluorescence of the marker is done by means of light, and the detection device must have a light source of adequate intensity, in order to penetrate the tissue to be examined to a depth of from 0.5 to 1 cm. In addition, an optical detector is necessary that on the one hand is capable of detecting the fluorescent light and on the other, if the fluorescent light is not in the visible wavelength range, also to record an image in the visible wavelength range.

In the prior art, fluorescence scanners are known which use a beam splitter for recording both an optical image and a fluorescence image. The beam splitter splits the beam of light, arriving from the object or body to be examined, into one beam whose spectrum is in the IR or NIR range of fluorescence and a beam in the visible wavelength range. The IR or NIR beam is carried to an image sensor, provided specifically for it, and the visible beam is carried to an image sensor suitable for it. The two image sensors, separately from one another, simultaneously record an image. Thus, the fluorescence image and the optical image are available and can be superimposed on one another. It is a disadvantage that two image sensors are required, and that the construction is relatively bulky.

Fluorescence scanners are also known in which there is a filter changer in the beam path prior to the image sensor. The filter changer changes to a specific filter for taking fluorescence images and a specific filter for taking optical images. At least for recording fluorescence images, a change must be made to a filter that filters out light in the visible wavelength range, because otherwise the fluorescent light would be washed out by the visible light. A disadvantage is that the filter changer is mechanically complicated and makes for a bulky construction. In addition, the optical and the fluorescence image must be taken in succession, which makes the recording more time-consuming and tends to promote artifacts in the image caused by scanner motion between obtaining the images.

SUMMARY

An image sensor includes an image detector and a filter layer, where the filter layer includes at least two different surface portions. The various surface portions have at least two kinds of different filter properties, and at least one surface portion is configured to allow fluorescent light to pass through and to filter out at least visible light. At least one surface portion is configured to allow visible light to pass through. As a result, the image sensor is suitable for recording both a visible optical and a fluorescence images contemporaneously or simultaneously. The image sensor may be for example, as a CCD camera and the image detector as a CCD chip, but other picture-taking technologies may be employed as well.

In an aspect, surface portions which allow fluorescent light to pass through and filter out visible light and surface portions which allow visible light to pass through are disposed alternately. In a further aspect, surface portions which allow visible light to pass through an at least partially attenuate fluorescent light. In this way, the optical image itself may be protected from becoming discolored or adulterated by fluorescent light.

In a yet another aspect, the dimensions of the surface portions of the filter match the dimensions of pixels of the image detector and are arranged congruently therewith. As a result, optimal resolution of both individual images may be obtained, since cross fading effects at intersecting surface portions and pixel boundaries may not occur.

In another aspect, the filter layer is disposed on a substrate layer, which in turn is disposed on the image detector. As a result, a production method, such as photolithography, may be used. Moreover, the substrate layer may also act as an adhesion-promoting layer for improving the adhesion of the filter layer.

BRIEF DESCRIPTION OF THE DRAWINGS

FIG. 1 is an application scenario for a fluorescence scanner according to one embodiment;

FIG. 2 is a perspective view of one embodiment of a fluorescence scanner with the outer housing open;

DETAILED DESCRIPTION

Figure 3:
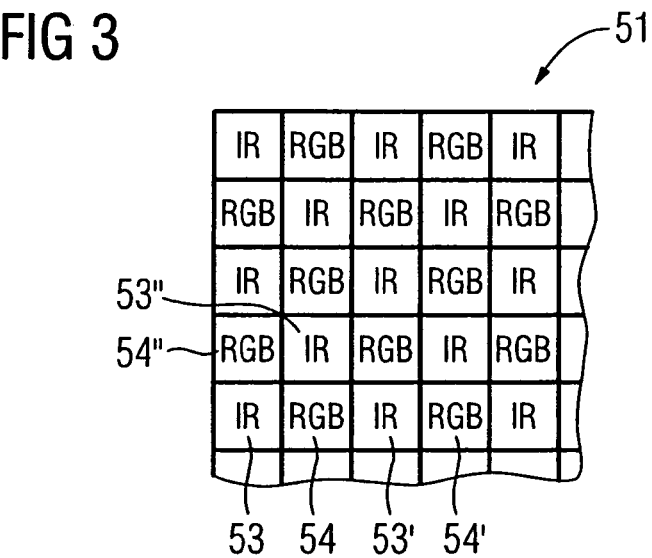
FIG. 3 is a schematic top view on an image sensor in one embodiment.

Exemplary embodiments may be better understood with reference to the drawings, but these embodiments are not intended to be of a limiting nature. Like numbered elements in the same or different drawings perform equivalent functions.

An image sensor for a fluorescence scanner for recording both optical and fluorescence images is described. The image sensor includes an image detector and a filter layer. The filter layer comprises at least two different surface portions, which have at least two kinds of different filter properties. At least one surface portion, for detecting infra-red (IR) or near-IR (NIR) light, has a filter characteristic such that fluorescent light can pass through, and at least visible light is filtered out or limited. "Filtered out" may or may not include complete removal. At least one further surface portion, for detecting visible light, has a filter characteristic such that visible light can pass through FIG. 1 schematically illustrates a scenario for using a fluorescence scanner 1. A body 4, to be examined, which may covered by an operating room (OR) drape 7, is lying on an operating table 5. A surgeon 3 is treating a region of the body 4 through an opening in the OR drape 7. The surgeon 3 holds a fluorescence scanner 1 in his hand, and with it, he can examine the body region to be treated.

The region 8 to be examined of the body 4 is shown schematically and enlarged. The body 4 may be covered, by the OR drape 7, except for an opening in the OR drape 7. The surgeon 3 aims the fluorescence scanner 1 centrally at the body region 8, which can be seen and reached through the opening.

Data detected by the fluorescence scanner 1 are typically transmitted in cordless fashion, to a personal computer (PC) workstation 9. The PC workstation 9 displays the data received, which are image data of the body region 8 to be examined, on a screen. The surgeon 3 may view the fluorescence scan on the screen of the PC workstation 9 and thus has the outcome of the scan immediately available for viewing. The surgeon can plan the surgical strategy or planning to the fluorescence scan, as needed.

To enable orientation to the image shown, the optical view of the fluorescence scan has a view of the same visible region or the same body region 8 superimposed thereon, in the form of a normal image in the visible wavelength range. Based on the image obtained in the visible wavelength range, the physician can recognize details of the body region 8 on the screen, and from the superimposed fluorescence scan, can associate the features shown on the scan with the visible features in the body region 8. Superimposition of an image made in the visible wavelength range permits the association with physical features even if the fluorescence is in a non-visible wavelength range, such as IR.

In FIG. 2, a fluorescence scanner 1 is shown in a perspective view. The upper covering of the housing has been omitted. The fluorescence scanner 1 has a handle 16 so that the scanner can be manipulated by the surgeon. On the handle 16, there is a button 17, with which the physician can manually initiate a fluorescence scan.

In the front region, excitation light sources 11, 11', 11", 11''' are arranged such that they may illuminate a region at a distance of approximately 6 to 10 cm. For that purpose, they are arranged at an angle of approximately 45° to the front panel. This arrangement may correspond to an optimal working distance, where the scanning region is not contacted by the scanner, and the distance is small enough to avoid the need for an excessively high excitation light intensity.

The excitation light sources 11, 11', 11", 11''' may be based on halogen light sources, and may be LEDs (light emitting diodes), laser diodes, and the like. Since an individual LED has a relatively low luminous intensity, LED arrays may be used for each light source. Each of the four LED arrays may have a luminous power of approximately 0.25 to 1 Watt.

A lens 12 is aimed frontally at the illuminated region, and by means of this lens, not only fluorescent light but also normal light and ambient light reach the fluorescence scanner 1. After passing through the lens, the incoming light passes through a filter 13, which filters out interfering light components not needed for the fluorescence scan. Light that has passed through the filter 13 reaches a CCD camera 15. The CCD camera 15 is capable of recording images both in the wavelength range of visible light and in the wavelength range of the fluorescence. The image data recorded by the CCD camera 15 are received by a data acquisition unit 14 and transmitted to the outside, preferably in cordless fashion.

FIG. 3 shows an example of an image sensor that can be used in the fluorescence scanner 1 described above and is shown in a schematic top view. The surface of the image sensor is divided up into many approximately square surface portions 53, 54, 53', 54', . . . , which form a filter layer 51. Each of the adjacently located surface portions 53, 54, 53', 54', . . . may have different filtering properties.

The surface portions 53, 53', 53", . . . are intended to allow light in the IR or NIR wavelength range to pass through, and are marked "IR" in the drawing. The filter characteristic of the surface portions 53, 53', 53", . . . does not allow light in the wavelength range of visible light to pass through or limits such light, as the IR or NIR fluorescent light would be washed out. Depending on the recording spectrum of the image detector located beneath the filter layer 51, which is not further visible in FIG. 3, not only visible light but also other wavelengths can be filtered out. The surface portions 53, 53', 53", . . . pass IR optical energy and permit recording of fluorescence images. The surface portions (53, 53', . . . ), which allow fluorescent light to pass through and filter out visible light may be one or more of $SiO_2$, $TiO_2$, $Ta_2O_5$, $HfO_2$ or $Al_2O_3$. The filter layer 51 has a layer thickness in the nanometer range, and may be in the range of few nm to approximately 1 μm. Each of the surface portions has a typical size of approximately 1 μm.

The surface portions 54, 54', 54", . . . may allow light in the visible wavelength range to pass through. In accordance with a typical way of recording or displaying color images, visible light can be considered as being composed of red (R), yellow (G) and blue (B) components, and the surface portions are therefore marked "RGB" in the drawing. In an aspect, the RGB surface portions 54, 54', 54", . . . are formed by cutouts out of the filter layer 51; the presence of no filter material meets the requirement that visible light must be capable of passing through. In a further aspect, the portions are formed by a material which results in essentially no filtering. In still another aspect, RGB surface portions are formed by a material whose filter characteristic is such that it filters out light in the IR or NIR range. In this way, the visible light passed through can be prevented from being discolored by fluorescent light or its spectrum adulterated. The surface portions 54, 54', 54", . . . pass visible light and permit the recording of a visible spectrum image.

The image sensor shown in FIG. 3 may record both an optical image and a fluorescence image simultaneously, each with half the resolution, compared with the highest possible resolution of the entire arrangement.

Figure 4:
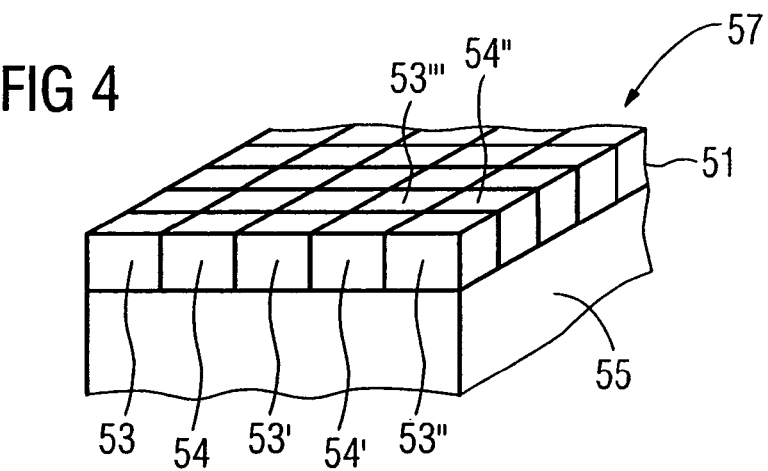
FIG. 4 is a schematic, perspective view of an embodiment of an image sensor.

In FIG. 4, a schematic, perspective view of an image sensor for use in the fluorescence scanner 1 is shown. The image sensor is embodied as a CCD element 57. The image sensor comprises a CCD chip 55, onto which a filter layer 51 that is composed of many approximately square surface portions 53, 54, 53', 54', . . . is applied. Adjacent surface portions 53, 54, 53', 54', . . . each have either an IR or an RGB filter characteristic. In the figure, the image sensor is meant to be used such that light coming from above is recorded for making a fluorescence scan first passes through the filter layer and then is detected by the CCD chip 55.

Respective adjacent regions of the CCD chip 55 that are located below adjacent surface portions 53, 54, 53', 54', . . . of the filter layer 51 are reached by either IR or NIR light or by visible light. Adjacent regions each record respective parts of an optical or a fluorescence image. The adjacent regions of the CCD chip 55 can each include a plurality of CCD pixels, or they may each be formed by individual CCD pixels.

The number of CCD pixels that are included depends on the dimensions of the surface portions 53, 54, 53', 54', . . . in the filter layer 51. The individual surface portions may be small enough to assure the desired resolution of the fluorescence scan. On the other hand, minimal limits for the dimensions are determined at least by the structuring process. Small dimensions can be achieved by means of a photolithographic structuring process. When the dimensions of the surface portions 53, 54, 53', 54', . . . are relatively small, more consideration should be to the congruence of the surface portions 53, 54, 53', 54', . . . which may each be located above individual pixels of the CCD chip 55. Small dimensions may result in cross fading effects if the surface portions 53, 54, 53', 54', . . . are not located substantially congruent with the CCD pixels.

To generate either an optical or a fluorescence images based on the image information recorded by the above-described image sensor, the RGB pixel regions or the IR pixel regions separately read out from the CCD chip 55. If a fluorescence scan is to result in a superimposed view of an optical and a fluorescence image, a separate readout of individual pixels may not be needed. Reading out all of the CCD pixels, because of the selected arrangement, may directly lead to the desired superimposed view (fusion). It is thus possible, with a single recording step, for example by actuating with the button 17 on the fluorescence scanner 1 as described earlier above, to generate one complete fluorescence scan. The relative intensity of the pixel outputs in the visible and the fluorescence wavelengths may be separately adjusted prior to forming the displayed composite image.

Figure 5:
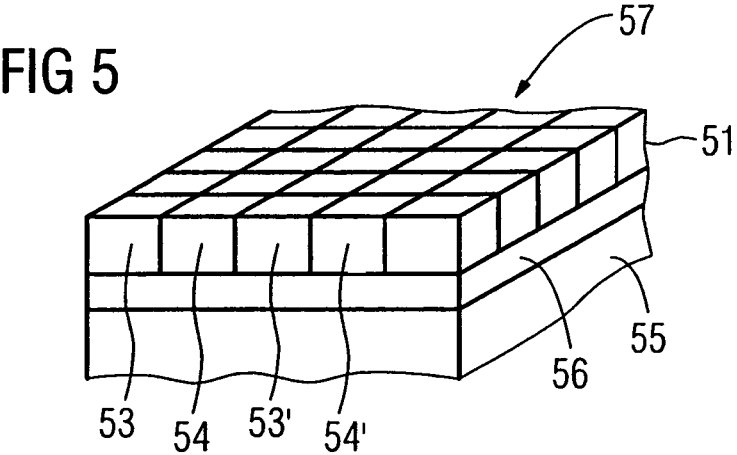
FIG. 5 is a schematic, perspective view of one embodiment of an image sensor with a substrate layer.

In FIG. 5, a schematic, perspective view of an image sensor for use in the fluorescence scanner 1 is shown with a substrate layer 56. The filter layer 51 is composed of IR and RGB surface portions 53, 54, 53', 54', . . . , as previously described. The surface portions are applied directly to the substrate layer 56 by, for example, photolithography. The substrate layer 56 may be optimized from the standpoint of adhesion of the filter layer 51. When applying the filter layer 51, coating and structuring processes that are may not be compatible with direct application to the CCD chip 55 may be used.

The substrate layer 56 may be applied directly to the CCD chip 55, for example by a coating process, or it may act as an independent load-bearing layer, onto which the filter layer 51 is first applied, and which is then mounted on the CCD chip. In an aspect, the substrate layer 56 is a glass layer, onto which the filter layer 51 is first applied and the glass layer then glued to the CCD chip 55 by means of an optical adhesive.

Figure 6:
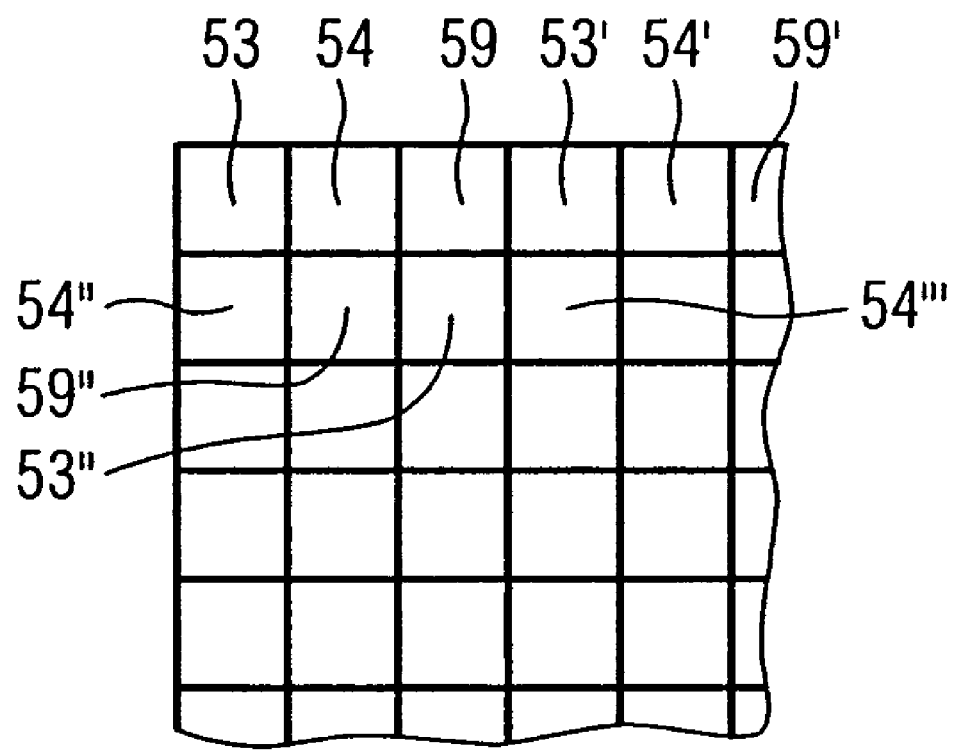
FIG. 6 is a schematic, perspective top view on a further embodiment of an image sensor.

In FIG. 6, a schematic, perspective top view is shown of a further example of an image sensor for use in the fluorescence scanner 1. In addition to the IR surface portions 53, 53', 53", . . . and the RGB surface portions 54, 54', 54", . . . , additional surface portions 59, 59', 59", . . . are provided, which can have still other filter properties. For example, they can be used for implementing a further detection method, or they can serve to supplement the IR or RGB surface portions 53, 54, 53', 54', . . . such that the different filter characteristics of the various surface portions 53, 54, 59, 53', 54', 59', . . . supplement one another.

The above-described arrangement of the various surface portions 53, 54, 59, 53', 54', 59', . . . along with their dimensions are understood to be only examples and can be varied as needed. For example, they certainly need not be square but can have other shapes instead. Moreover, they certainly need not be located in alternating fashion and/or in even numbers; sequences are instead conceivable in which larger IR regions alternate with smaller RGB regions, in order to take appropriate account of the lesser intensity of the IR light.

Although only a few exemplary embodiments have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

The invention claimed is:

1. A fluorescence scanner, comprising:
an image detector; and
a filter layer fixedly disposed with respect to the image detector;
wherein the filter layer has a plurality of first portions and second portions; the first portions pass fluorescent light while filtering out at least visible light, and each of the second portions is an RGB filter; and, the first and the second filter portions are alternately disposed with respect to each other in a horizontal and a vertical direction of a surface of the filter layer.

2. The fluorescence scanner of claim 1, wherein one of the first or the second portions is made of $SiO_2$, $TiO_2$, $Ta_2O_5$, $HfO_2$, $Al_2O_3$ or combinations thereof.

3. The fluorescence scanner of claim 1, wherein the filter layer has a layer thickness approximately several nm to approximately 1 μm.

4. The fluorescence scanner of claim 1, wherein the second portions attenuate fluorescent light.

5. The fluorescence scanner of claim 1, wherein each of the first and the second portions have a planar peripheral side size of approximately 1 μm.

6. The fluorescence scanner of claim 1, wherein the image detector is a charge coupled device (CCD) chip.

7. The fluorescence scanner of claim 6, wherein the filter layer is disposed on a substrate layer, the substrate layer being disposed on the image detector and wherein the substrate layer is a glass.

8. The fluorescence scanner of claim 1, wherein the filter layer is disposed on a substrate layer, the substrate layer being disposed on the image detector.

9. The fluorescence scanner of claim 1, wherein the substrate layer is a glass.

10. The fluorescence scanner of claim 1, wherein the filter layer has a layer thickness approximately several nm to approximately 1 μm.

11. The fluorescence scanner of claim 10, wherein each of the first and the second portions have a planar peripheral side size of approximately 1 μm.

12. The fluorescence scanner of claim 1, further comprising an actuation button, wherein the actuation of the actuation button results in generation of an exciting light by the light source and the contemporaneous recording of optical and fluorescent images.

13. The fluorescence scanner of claim 1, where the optical and fluorescent images are recorded simultaneously.

* * * * *